United States Patent
Oka et al.

(10) Patent No.: US 9,408,752 B2
(45) Date of Patent: Aug. 9, 2016

(54) X-RAY DETECTABLE ADHESIVE BANDAGE AND METHOD OF MANUFACTURING X-RAY DETECTABLE ADHESIVE BANDAGE

(75) Inventors: Keiji Oka, Shiga (JP); Akihiro Yamaguchi, Tokyo (JP)

(73) Assignee: PIAC CO., LTD., Shiga (JP)

( * ) Notice: Subject to any disclaimer, the term of this patent is extended or adjusted under 35 U.S.C. 154(b) by 434 days.

(21) Appl. No.: 14/006,383

(22) PCT Filed: Jul. 3, 2012

(86) PCT No.: PCT/JP2012/066929
§ 371 (c)(1),
(2), (4) Date: Sep. 20, 2013

(87) PCT Pub. No.: WO2013/005728
PCT Pub. Date: Jan. 10, 2013

(65) Prior Publication Data
US 2014/0012175 A1  Jan. 9, 2014

(30) Foreign Application Priority Data
Jul. 4, 2011  (JP) ................................. 2011-148420

(51) Int. Cl.
*A61F 13/02* (2006.01)
*A61F 13/44* (2006.01)
*A61F 13/00* (2006.01)

(52) U.S. Cl.
CPC .............. *A61F 13/0259* (2013.01); *A61F 13/02* (2013.01); *A61F 13/0289* (2013.01); *A61F 13/44* (2013.01); *A61F 2013/00936* (2013.01); *Y10T 156/1052* (2015.01)

(58) Field of Classification Search
CPC .......... A61F 13/02; A61F 13/00; A61F 13/44; A61F 2013/00936; A61F 13/0259; A61F 13/0289; A61F 13/0203; A61F 2013/00748; A61F 13/105; Y10T 156/1052
See application file for complete search history.

(56) References Cited

FOREIGN PATENT DOCUMENTS

| GB | 1381855 | 1/1975 |
|----|---------|--------|
| GB | 2308308 | 6/1997 |
| JP | 3025216 | 3/1996 |
| JP | 10-502277 | 3/1998 |
| WO | WO 2008/146529 A1 | 12/2008 |

OTHER PUBLICATIONS

European Search Report dated Mar. 20, 2015, for European Patent Application No. 12808003.3.

*Primary Examiner* — Ophelia A Hawthorne
(74) *Attorney, Agent, or Firm* — Fitch, Even, Tabin & Flannery LLP

(57) ABSTRACT

An X-ray detectable adhesive bandage includes: an adhesive protective member further including a substrate and an adhesive layer; and an absorbent member formed by layering, in order from bottom to top, at a prescribed site upon the adhesive protective member, a metallic foil further including a hot melt bonding agent layer, a long object which is formed by an X-ray detectable material being covered either in whole or in part by a covering object, and an absorbent pad. The absorbent member is configured from a prescribed metallic foil, a prescribed long object, and an absorbent pad such as a heat bonding layered body.

8 Claims, 8 Drawing Sheets

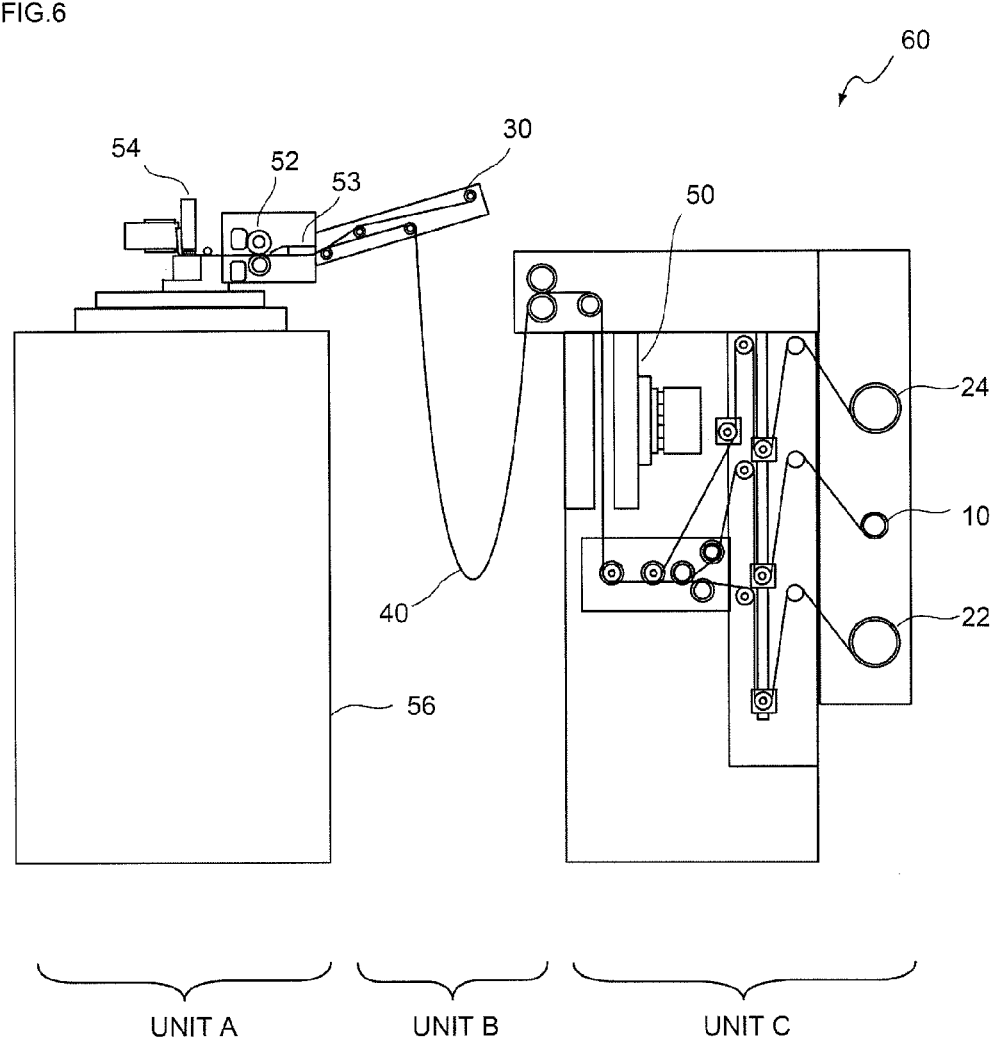

X-RAY DETECTABLE ADHESIVE BANDAGE AND METHOD OF MANUFACTURING X-RAY DETECTABLE ADHESIVE BANDAGE

BACKGROUND OF THE INVENTION

1. Field of the Invention

The invention relates to an X-ray detectable adhesive bandage and a method of manufacturing an X-ray detectable adhesive bandage. More specifically, the invention relates to an X-ray detectable adhesive bandage detectable with high accuracy by an X-ray inspection apparatus, and to a method of manufacturing such an X-ray detectable adhesive bandage.

2. Description of the Related Art

In the prior art, there are proposed adhesive bandages that are detectable by a metal detector in case they are accidentally placed in food products or other products.

More specifically, as shown in FIG. 8A, a first-aid adhesive bandage 110 includes a pressure-sensitive adhesive sheet 102, an aluminum foil 105 and a pad 103 which are provided on the pressure-sensitive adhesive sheet 102, wherein the aluminum foil 105 is interposed between the pressure-sensitive adhesive sheet 102 and the pad 103 (see, for example, Patent Document 1).

There are also proposed an X-ray detectable material-bearing fabric and an X-ray detectable adhesive bandage, which are detectable with high accuracy, and a method of manufacturing such an X-ray detectable adhesive bandage (see, for example, Patent Document 2).

More specifically, as shown in FIG. 8B, an X-ray detectable adhesive bandage 230 includes a pressure-sensitive adhesive protective member 216 including a backing 214 and a pressure-sensitive adhesive layer 212; and an absorbent pad 220 provided on a predetermined part of the pressure-sensitive adhesive protective member 216, wherein the absorbent pad 220 includes an X-ray detectable material-bearing fabric 206 composed of a fabric 210 (210a, 210b), a cover material 204, and X-ray detectable materials 202 arranged at predetermined intervals and entirely or partially covered with the cover material 204.

PRIOR ART DOCUMENTS

Patent Document

[Patent Document 1] JP3025216U (UTILITY MODEL, Claims)

[Patent Document 2] WO2008/146529A (Claims)

SUMMARY OF THE INVENTION

Unfortunately, the first-aid adhesive bandage disclosed in Patent Document 1 (utility model) has a problem in that the aluminum foil is too thin to be detected by an X-ray inspection apparatus although it is detectable by a metal detector.

The X-ray detectable material-bearing fabric disclosed in Patent Document 2 has a problem in that the manufacturing steps are relatively complicated and thus may have a low yield although it is detectable with high accuracy by an X-ray inspection apparatus.

For example, there is a problem in that when a specific X-ray detectable material-bearing fabric is interwoven between two fabrics by stitch bonding, the needle may be damaged by coming into contact with the X-ray detectable material.

There is also a problem in that in the cutting process, the cutting device may be damaged by coming into contact with the X-ray detectable material.

Thus, the inventors have accomplished the invention based on the finding that an absorbent member composed of a specific metal foil detectable by a metal detector, a long member containing an X-ray detectable material, and an absorbent pad could have high sensitivity to a metal detector and an X-ray inspection apparatus and that such an absorbent member could be stably manufactured by heat and pressure bonding.

Specifically, it is an object of the invention to provide an X-ray detectable adhesive bandage having high detection sensitivity not only to a metal detector commonly used but also to an X-ray inspection apparatus, and to provide a method for efficiently manufacturing such an X-ray detectable adhesive bandage.

To solve the above problems, the invention provides an X-ray detectable adhesive bandage including: a pressure-sensitive adhesive protective member (a protective member having a pressure-sensitive adhesive layer) including a backing and a pressure-sensitive adhesive layer; and an absorbent member that is provided on a predetermined part of the pressure-sensitive adhesive protective member and includes a metal foil provided with a hot melt adhesive layer, a long member including a cover material and an X-ray detectable material entirely or partially covered with the cover material, and an absorbent pad, wherein the metal foil, the long member, and the absorbent pad are sequentially stacked from bottom to top, wherein the absorbent member includes a heat and pressure bonded laminate of the metal foil provided with the hot melt adhesive layer, the long member including the cover material and the X-ray detectable material entirely or partially covered with the cover material, and the absorbent pad.

Specifically, the X-ray detectable material entirely or partially covered with the cover material is prevented from moving from the placed position and is less likely to drop out or move. Thus, when the X-ray detectable adhesive bandage, which may include an X-ray detectable material-bearing fabric according to the invention, is accidentally placed in a packaged metal product, it could be accurately detected by an X-ray inspection apparatus although it is not detectable by a metal detector.

The long member having the X-ray detectable material covered with the cover material, the specific metal foil, and the absorbent pad are sequentially stacked to form an absorbent member, and the absorbent member is subjected to heat and pressure bonding. This makes it possible to omit a process involving the use of an interweaving apparatus and to effectively prevent a cutting device from being damaged by the X-ray detectable material.

In addition, the absorbent member having the specific metal foil has good sensitivity not only to an X-ray inspection apparatus but also to a metal detector, which makes it possible to further increase the sensitivity for detection of the contamination of food products or other products.

In the invention, the heat and pressure bonded laminate corresponds to the absorbent member obtained by sequentially stacking the specific metal foil, the specific long member, and the absorbent pad and subjecting the stacked materials to heat and pressure bonding.

In forming the X-ray detectable adhesive bandage of the invention, the X-ray detectable material is preferably linear and preferably has an average length in the range of 0.3 mm to 10 mm and an average thickness in the range of 0.1 mm to 3 mm.

According to this feature, a desired level of sensitivity to an X-ray inspection apparatus could be obtained.

According to this feature, the X-ray detectable material is easily aligned in a plane direction, so that foreign body sensation could be reduced during use and degradation in the function of the absorbent pad could be minimized.

In forming the X-ray detectable adhesive bandage of the invention, the X-ray detectable material is preferably a coiled material.

According to this feature, damage to a cutting part during a cutting process could be further reduced without loss of sensitivity to an X-ray inspection apparatus.

In forming the X-ray detectable adhesive bandage of the invention, the metal foil is preferably made of aluminum.

According to this feature, a relatively-light, X-ray detectable adhesive bandage could be manufactured at low cost without loss of sensitivity to a metal detector.

In forming the X-ray detectable adhesive bandage of the invention, the metal foil preferably has a thickness in the range of 1 μm to 30 μm.

According to this feature, the adhesive bandage could keep stretch ability intact, have good comfortableness, keep intact sensitivity to a metal detector, and have formability.

In forming the X-ray detectable adhesive bandage of the invention, the hot melt adhesive is preferably at least one selected from the group consisting of an olefin-based hot melt adhesive, a polyethylene-based hot melt adhesive, a polypropylene-based hot melt adhesive, a polyester-based hot melt adhesive, and a polyvinyl chloride-based hot melt adhesive.

According to this feature, the specific metal foil, the specific long member, and the absorbent pad could be easily heat and pressure bonded, so that the resulting product could be less irritant to the skin and have good comfortableness.

In forming the X-ray detectable adhesive bandage of the invention, the backing in the pressure-sensitive adhesive protective member is preferably colored.

According to this feature, the adhesive bandage is easy to be visually identified even when accidentally placed in food products or other products. In particular, even when only the backing out of the pressure-sensitive adhesive protective member is accidentally placed in food products or other products, the backing could be easily visually detected.

Another aspect of the invention is a method of manufacturing an X-ray detectable adhesive bandage including: a pressure-sensitive adhesive protective member including a backing and a pressure-sensitive adhesive layer; and an absorbent member that is provided on a predetermined part of the pressure-sensitive adhesive protective member and includes a metal foil provided with a hot melt adhesive layer, a long member including a cover material and an X-ray detectable material entirely or partially covered with the cover material, and an absorbent pad, which are sequentially stacked from bottom to top, the method including the steps of: stacking a metal foil, a long member including a cover material and X-ray detectable materials entirely or partially covered with the cover material, and an absorbent pad to form an absorbent member; heating the absorbent member to integrate the stacked materials and to form a heat and pressure bonded laminate; cutting the heat and pressure bonded laminate into pieces of a predetermined size; forming a pressure-sensitive adhesive protective member; and laminating the heat and pressure bonded laminate onto a predetermined part of the pressure-sensitive adhesive protective member.

Specifically, the specific metal foil, the specific long member, and the absorbent pad are laminated and integrated by heat and pressure bonding, which makes possible to successfully fix the X-ray detectable material onto a predetermined part and to successfully manufacture the adhesive bandage without damage to a cutting device during a cutting process, so that the yield could be increased.

In addition, there is no need to interweave the specific long member into the absorbent pad, so that the process could be simplified and the productivity could be improved.

Also, because of the integration of the specific metal foil and the absorbent pad, an X-ray detectable adhesive bandage without loss of its stretchability could be efficiently obtained.

In addition, the combination of the X-ray detectable material and the specific metal foil could form an X-ray detectable adhesive bandage capable of well responding not only to an X-ray inspection apparatus but also to a metal detector.

BRIEF DESCRIPTION OF THE DRAWINGS

FIG. 6 is a diagram provided for illustrating a method of manufacturing an X-ray detectable adhesive bandage;

DETAILED DESCRIPTION OF THE EMBODIMENTS

First Embodiment

Figure 1A:
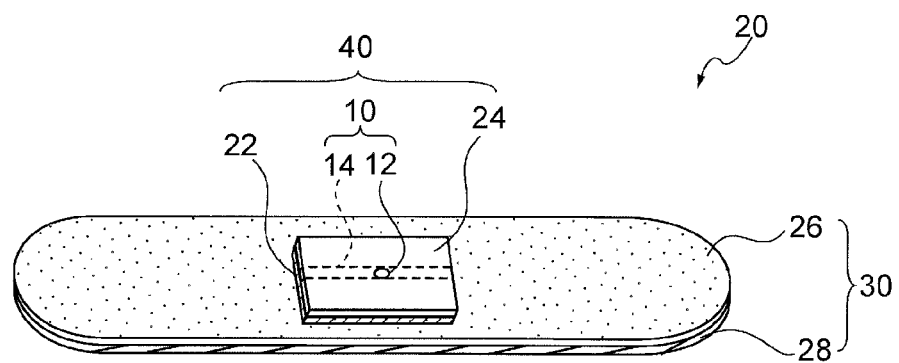
FIGS. 1A to 1B are diagrams for illustrating an aspect of an X-ray detectable adhesive bandage.
Figure 1B:
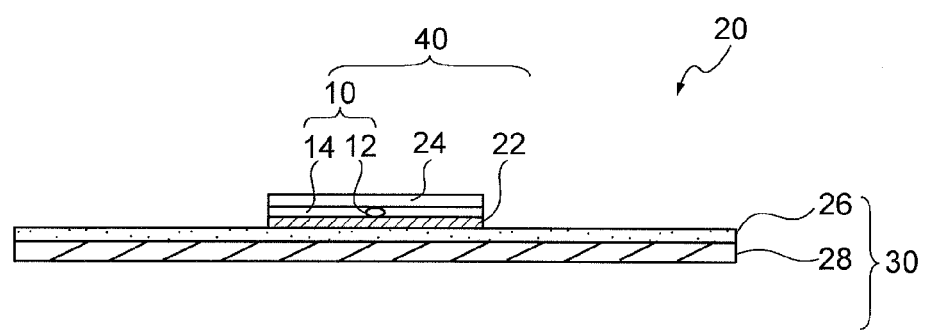

As shown in FIGS. 1A to 1B, a first embodiment of the invention is an X-ray detectable adhesive bandage 20 including: a pressure-sensitive adhesive protective member 30 including a backing 28 and a pressure-sensitive adhesive layer 26; and an absorbent member 40 that is provided on a predetermined part of the pressure-sensitive adhesive protective member and includes a metal foil 22 provided with a hot melt adhesive layer, a long member 10 including a cover material 14 and an X-ray detectable material 12 entirely or partially covered with the cover material 14, and an absorbent pad 24, wherein the metal foil 22, the long member 10, and the absorbent pad 24 are sequentially stacked from bottom to top, wherein the absorbent member 40 includes a heat and pressure bonded laminate of the metal foil 22 provided with the hot melt adhesive layer, the long member 10 including the cover material and the X-ray detectable material entirely or partially covered with the cover material, and the absorbent pad 24.

Hereinafter, the X-ray detectable adhesive bandage 20 of the first embodiment will be more specifically described for each constitutional feature.

1. Absorbent Member 1-1. Absorbent Pad

The absorbent pad constituting the X-ray detectable adhesive bandage may be of any type. For example, it is preferably an absorbent pad obtained by a dry staple method, an air lay process, a melt-blowing process, a needle punch method, a stitch bonding method, or a spun lace method.

For example, such an absorbent pad is preferably in the form of a nonwoven fabric composed of entangled short fibers with a length of 15 to 100 mm and a diameter of 6 to 100 μm.

Alternatively, for example, it is preferably in the form of a nonwoven fabric composed of long fibers with a length of 1 m to 100 m or more and short fibers with a length of 15 to 100 mm, which are entangled together.

The thickness of the absorbent pad (not being compressed) is preferably in the range of 0.1 to 10 mm, more preferably in the range of 0.5 to 3 mm, even more preferably in the range of 1 to 2.5 mm.

This is because if the absorbent pad has such a thickness, there could be a good balance between desired handleability and easiness of bonding to the long member and the metal foil.

Specifically, if the absorbent pad is too thin, its ability to absorb blood, body fluid or the like will be lowered, so that the function of the adhesive bandage may be degraded. In addition, if the absorbent pad is too thin, the X-ray detectable material may irritate the skin, so that comfortableness may decrease. On the other hand, if the absorbent pad is too thick, the absorbent pad may rather have lower handleability or lower adhesion to the metal foil and the long member.

The weight of the absorbent pad (not being compressed) is preferably in the range of 10 to 500 $g/m^2$, more preferably in the range of 30 to 300 $g/m^2$, even more preferably in the range of 50 to 150 $g/m^2$.

This is because if the absorbent pad has such a weight, there could be a good balance between desired handleability and easiness of bonding to the long member and the metal foil.

Specifically, if the absorbent pad is too light, the handleability of the absorbent pad may decrease, or the X-ray detectable material may irritate the skin, so that comfortableness may decrease. On the other hand, if the absorbent pad is too heavy, the handleability of the absorbent pad may rather decrease, or comfortableness may decrease.

The bulk density of the absorbent pad (not being compressed) is preferably in the range of 0.005 to 0.5 $g/cm^3$, more preferably in the range of 0.01 to 0.1 $g/cm^3$, even more preferably in the range of 0.05 to 0.08 $g/cm^3$.

This is because if the absorbent pad has such a bulk density, there could be a good balance between desired handleability and easiness of bonding to the long member and the metal foil.

Specifically, if the absorbent pad has a lower bulk density, the absorbent pad may have lower handleability or may have difficulty in absorbing blood or body fluid, and easiness of boding to the long member and the metal foil may decrease. On the other hand, if the absorbent pad has too high a bulk density, the absorbent pad may rather have lower handleability or difficulty in absorbing blood or body fluid.

The absorbent pad is preferably made of at least one type of fibers selected from the group consisting of polyester fibers, polyamide fibers, polyacrylic fibers, polyolefin fibers, polyurethane fibers, polyacetal fibers, polyvinyl alcohol fibers, rayon fibers, cotton fibers, pulp fibers, and polyvinyl chloride fibers.

This is because the absorbent pad made of any of these types of fibers is easy to be stably manufactured and has high ability to absorb body fluid and blood.

Particularly when the absorbent pad is made of a nonwoven fabric of a blend of rayon and polyester fibers, a blend of polypropylene and polyethylene fibers, or a blend of polypropylene and polyester fibers, a good balance between lightness and durability could be achieved.

The absorbent pad is preferably a laminate having a network film on the side to be in contact with the skin.

This is because such a network film could prevent the absorbent pad from excessively adhering to the skin or prevent the absorbent pad from solidifying together with body fluid or blood and adhering to wound, and because such a network film is sanitary.

Such a network film is preferably made of at least one film selected from the group consisting of a polyethylene film, a polypropylene film, a polyester film, a polyamide film, a polyacrylic film, a polyolefin film, a polyurethane film, a polyacetal film, a polyvinyl alcohol film, a rayon film, a cotton film, a pulp film, and a polyvinyl chloride film.

This is because the network film made of such a type of film is easy to be stably manufactured and could make the product less irritant to the skin.

In particular, a sanitary network film could be obtained with high productivity if a polyethylene film or a polypropylene film is used to form the network film.

1-2. Long Member

As shown in FIGS. 2A to 2B or FIGS. 3A to 3D, X-ray detectable materials 12 may be arranged at predetermined intervals (L) and entirely or partially covered with a cover material 14 (14a, 14b).

Figure 2A:
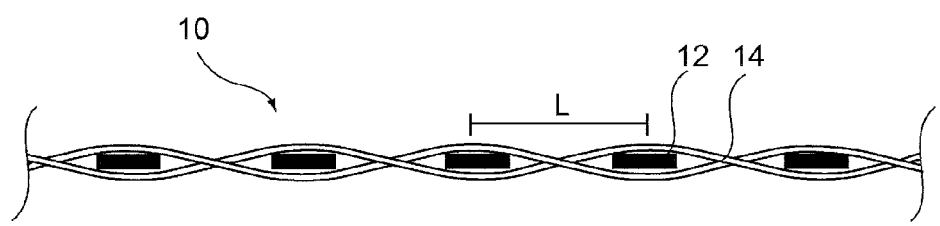
FIGS. 2A to 2B are diagrams for illustrating an aspect of a long member containing X-ray detectable materials arranged at predetermined intervals and covered with a cover material.

FIG. 2A is a schematic cross-sectional view of a long member 10, which includes substantially cylindrical (hereinafter, also called "linear") X-ray detectable materials 12 arranged at regular intervals and surrounded and covered with a cover material 14 including a plurality of fibrous materials (fibers).

Figure 2B:
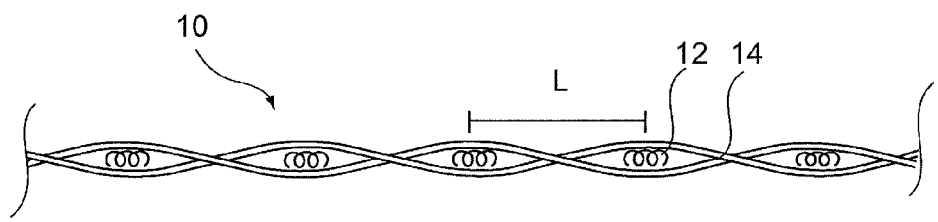

FIG. 2B is a schematic cross-sectional view of a long member 10, which includes substantially coiled X-ray detectable materials 12 arranged at regular intervals and surrounded and covered with a cover material 14 including a plurality of fibrous materials (fibers).

Figure 4A:
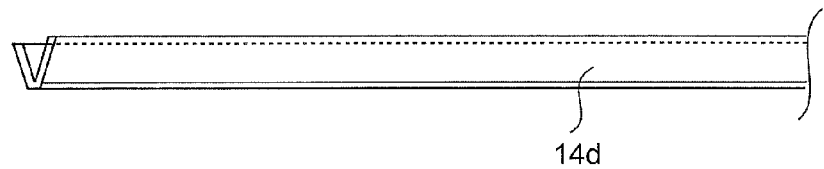
FIGS. 4A to 4C are diagrams provided for illustrating a preferred aspect of the long member shown in FIG. 2B.
Figure 4B:
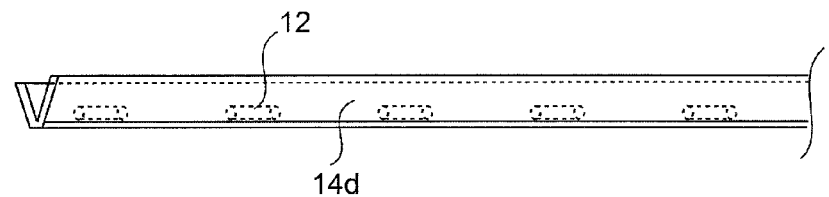
Figure 4C:
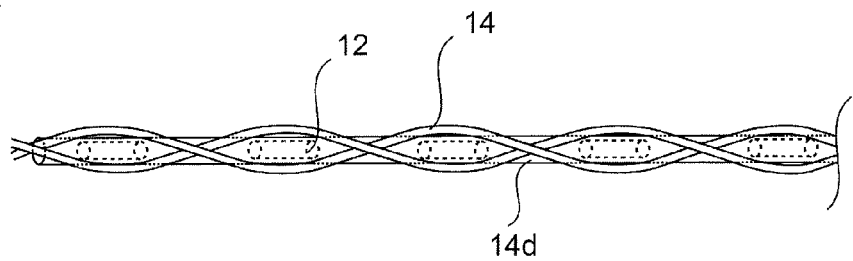

In some cases, X-ray materials 12 covered with a cover material 14 including a plurality of fibrous materials (fibers) as shown in FIGS. 2A to 2B may tend to drop out of the cover material. In a preferred mode, therefore, as shown in FIGS. 4A to 4C, a film 14d formed (folded) in a V shape is first prepared, and X-ray detectable materials 12 are placed at the bottom of the V-shaped film 14d, and surrounded and covered in this state with a cover material 14 including fibrous materials (fibers).

Figure 3A:
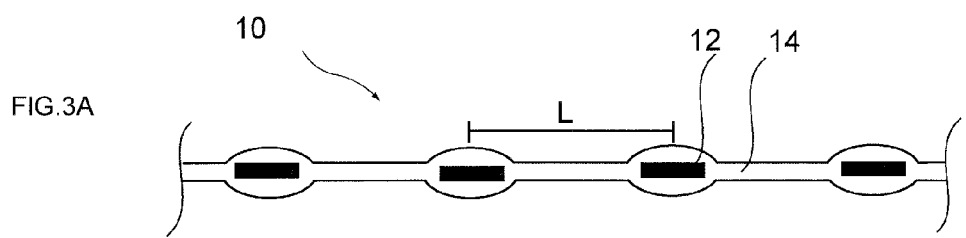
FIGS. 3A to 3D are diagrams provided for illustrating another aspect of a long member containing X-ray detectable materials arranged at predetermined intervals and covered with a cover material.

FIG. 3A is a schematic cross-sectional view of a long member 10, which includes substantially cylindrical X-ray detectable materials 12 arranged at regular intervals and covered from upper and lower sides with a cover material 14.

Figure 3B:
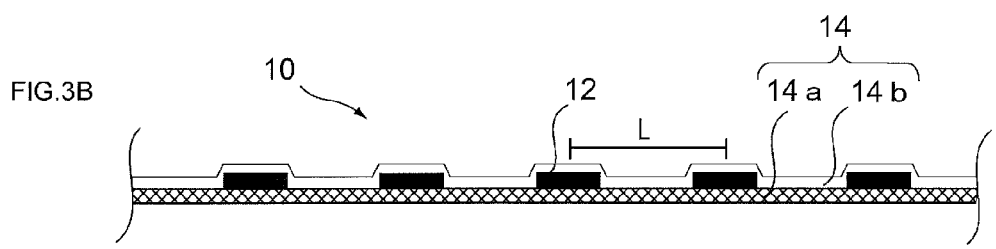

FIG. 3B is a schematic cross-sectional view of a long member 10, which includes substantially rectangular X-ray detectable materials 12 that are arranged at regular intervals, disposed on a cover material-forming base 14a as a part of a cover material 14, and covered from upper side with a cover material-forming resin 14b as an another part of the cover material 14.

Examples of the form of the cover material-forming base 14a shown in FIG. 3B include, but are not limited to, a PET film, an acrylic film, a urethane foam, a polyethylene foam, a silicone rubber, a natural rubber, etc.

Figure 3C:
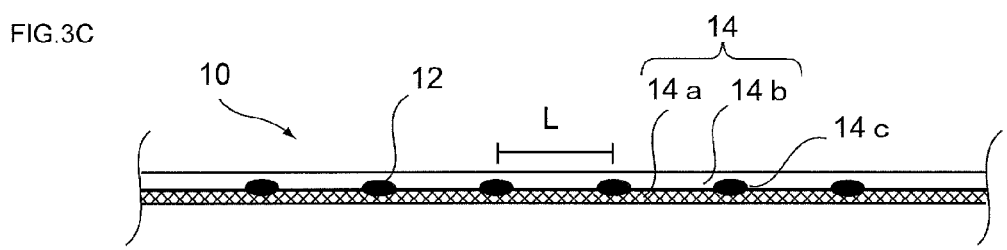

FIG. 3C is a schematic cross-sectional view of a long member 10, which includes substantially flat (elliptical) X-ray detectable materials 12 that are arranged at regular intervals, embedded in the interior 14c of a cover material-forming base 14a as a part of a cover material 14, and covered from upper side with a cover material-forming resin 14b as another part of the cover material 14.

Figure 3D:
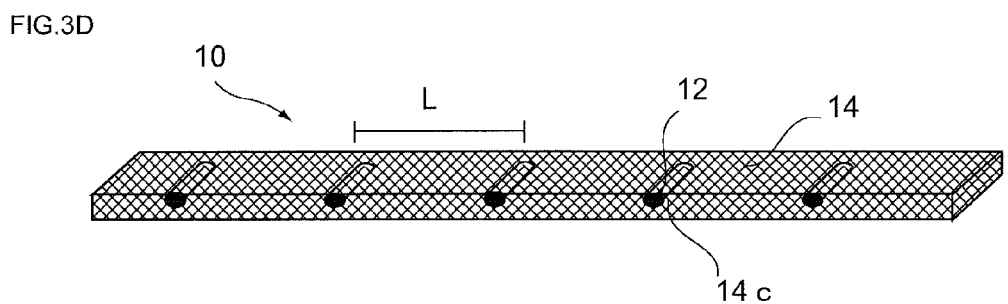

FIG. 3D is a schematic cross-sectional view of a long member 10, which includes substantially cylindrical X-ray detectable materials 12 that are embedded in the interior 14c of a cover material 14, specifically, partially covered with the cover material 14, and are arranged at regular intervals in such a manner that their longitudinal directions are perpendicular to the interval.

Specifically, as shown in FIGS. 2A to 2B or FIGS. 3A to 3D, X-ray detectable materials 12 may be covered with a cover material to form a desired long member 10, and the long member 10 may be cut into pieces of a predetermined length, so that long members with no variations in sensitivity to an X-ray inspection apparatus could be obtained.

In addition, when X-ray detectable materials are discontinuously arranged at regular intervals to form a specific long member 10 as shown in FIGS. 2A to 2B or FIGS. 3A to 3D, the resulting X-ray-detectable-material-containing long member could form adhesive bandages without loss of stretchability.

In the specific long member 10 shown in FIG. 2A or other drawings, the X-ray detectable materials 12 covered with the cover material 14 are preferably arranged at regular intervals (L) ranging from 3 to 60 mm.

Thus, the specific distance (pitch) between adjacent X-ray detectable materials incorporated in the long member is preferably in the range of 3 to 60 mm, more preferably in the range of 5 to 40 mm, even more preferably in the range of 8 to 30 mm.

This is because such a structure makes it possible to effectively prevent X-ray detectable materials from deviating from a predetermined position.

In addition, when there is such a distance between adjacent X-ray detectable materials, not only the position where X-ray detectable materials exist but also the position where no X-ray detectable materials exist could be accurately identified. This makes it possible to prevent the cutting machine from being damaged.

Thus, dislocation of X-ray detectable materials could be effectively prevented by laminating such a specific long member, a specific metal foil, and an absorbent pad. As a result, the sensitivity to an X-ray inspection apparatus could be reliably increased.

In addition, when such X-ray detectable materials are arranged at regular intervals, namely, when interruptions are provided, the resulting long member could form adhesive bandages without loss of stretchability.

1-3. X-Ray Detectable Material (1) Shape

The shape of the X-ray detectable material is preferably, but not limited to, a linear shape as shown in FIG. 2A.

Such linear X-ray detectable materials preferably have an average length in the range of 0.3 to 10 mm and an average thickness (diameter) in the range of 0.1 to 3 mm.

Such a structure makes it possible to provide higher detection sensitivity to an X-ray inspection apparatus or a metal detector and to minimize the reduction in the function of the absorbent pad.

Thus, the average length of linear X-ray detectable materials incorporated in the long member is more preferably in the range of 0.5 to 5 mm, even more preferably in the range of 1 to 3 mm.

The average thickness is more preferably in the range of 0.5 to 2.5 mm, even more preferably in the range of 1 to 2 mm.

The linear X-ray detectable material is also preferably coiled as shown in FIG. 2B.

Such a structure will not reduce the detection sensitivity to an X-ray inspection apparatus or a metal detector and could prevent a cutting part from being damaged even when the material accidentally comes into contact with the cutting part during the cutting process.

The X-ray detectable materials may have a spherical shape, a rectangular shape as shown in FIG. 3B, or a flat shape as shown in FIG. 3C.

For example, spherical X-ray detectable materials preferably have an average particle size (sphere equivalent diameter) in the range of 0.1 to 3 mm.

This is because if the average particle size of such X-ray detectable materials is below 0.1 mm, the detection sensitivity to an X-ray inspection apparatus or a metal detector may significantly decrease, and on the other hand if the average particle size of such X-ray detectable materials is above 3 mm, the use of them for the absorbent pad or the like of an adhesive bandage may increase foreign body sensation, or it may become difficult to stably incorporate them into the long member.

Thus, the average particle size (sphere equivalent diameter) of X-ray detectable materials incorporated in the long member is more preferably in the range of 0.1 to 2 mm, even more preferably in the range of 0.2 to 1 mm, most preferably in the range of 0.3 to 0.8 mm.

(2) Type

The X-ray detectable material is preferably at least one selected from the group consisting of steel (including a steel-plated material), stainless steel, aluminum, copper, silver, solder (including lead-free solder), nickel, bone, a rubber piece, a resin piece, a glass, a shell, and a stone.

This is because the use of such X-ray detectable materials makes it possible to further increase the sensitivity to an X-ray inspection apparatus and also makes it possible to provide relatively inexpensive X-ray detectable adhesive bandages easily workable into desired shapes.

Even nonmetallic materials such as bone, rubber piece, resin piece, glass, shell, and stone, which have certain densities, could not only provide certain sensitivity to an X-ray inspection apparatus but also form X-ray detectable adhesive bandages while being lightweight.

It will be understood that steel (including a steel-plated material) is more preferably used as the X-ray detectable material because steel is ferromagnetic so that it could provide higher sensitivity to an X-ray inspection apparatus or a metal detector, and is also inexpensive.

Although steel is usually rust-prone depending on environmental conditions, it has been found that steel in the long member according to the invention hardly rusts because it is surrounded by the cover material under dry conditions.

A steel-plated material or stainless steel is also preferably used because it could give a certain level of sensitivity to an X-ray inspection apparatus or a metal detector over a long period of time and could be easily incorporated into the long member.

On the other hand, to minimize foreign body sensation for the adhesive bandage, at least one of bone, rubber piece, resin piece, glass, shell, stone, aluminum, copper, silver, and solder (including lead-free solder) is preferably used. This is because any of these nonmetallic or metallic materials could be easily deformed by application of a certain level of force.

As a non-limiting example, the substantially rectangular X-ray detectable materials 12 shown in FIG. 3B could be obtained by cutting a metal foil or plate with a uniform thickness into pieces of a predetermine width.

For example, the flat (elliptical) X-ray detectable materials 12 shown in FIG. 3C are preferably formed by flattening relatively-soft spherical particles of aluminum, copper, steel, solder, or other materials.

For example, the substantially cylindrical X-ray detectable materials 12 shown in FIG. 3D are preferably formed by cutting a metal wire into pieces of a predetermined length.

1-4. Cover Material

The cover material is preferably made of at least one type of fibers selected from the group consisting of polyester fibers, polyamide fibers, polyacrylic fibers, polyolefin fibers, polyurethane fibers, polyacetal fibers, polyvinyl alcohol fibers, rayon fibers, cotton fibers, pulp fibers, and polyvinyl chloride fibers.

This is because such fibers could be easily turned into a fabric and also allows easy detection of the X-ray detectable materials.

For example, the fibers preferably have a thickness (diameter) in the range of 10 to 100 μm. A plurality of such fibers may be gathered and twisted.

1-5. Metal Foil (1) Type

Examples of metal used to form the specific metal foil include, but are not limited to, aluminum, copper, stainless steel, nickel, tin, gold, silver, titanium, etc.

This is because such types of metals could form metal foils detectable with high sensitivity by a metal detector.

In particular, the metal is preferably aluminum.

This is because the metal foil made of aluminum is inexpensive, has high productivity, and could form an X-ray detectable adhesive bandage without excessive loss of stretchability when it is laminated together with the absorbent pad and the specific long member.

(2) Thickness

The thickness of the metal foil is preferably in the range of 1 to 30 μm.

This is because if the metal foil has a thickness of below 1 μm, it may have significantly low sensitivity to a metal detector or may be easily ruptured. On the other hand, if the metal foil has a thickness of above 30 μm, the metal foil may be difficult to be stably laminated to the specific long member and the absorbent pad, or foreign body sensation may increase.

Thus, the thickness of the metal foil is more preferably in the range of 2 to 30 μm, even more preferably in the range of 10 to 20 μm.

(3) Adhesive Layer

In the invention, the metal foil is characterized in that at least one side of the metal foil is provided with a hot melt adhesive layer.

This is because such a structure could be easily bonded to the specific long member and the absorbent pad to form an integrated member and could provide high productivity.

For example, the hot melt adhesive is preferably, but not limited to, at least one selected from the group consisting of an olefin-based hot melt adhesive, a polyethylene-based hot melt adhesive, a polypropylene-based hot melt adhesive, a polyester-based hot melt adhesive, and a polyvinyl chloride-based hot melt adhesive.

This is because such an adhesive could easily bond the specific long member and the absorbent pad to form an integrated member, and is less irritant to the skin.

The hot melt adhesive layer is preferably applied so as to have a thickness in the range of 0.001 to 0.5 μm.

2. Pressure-Sensitive Adhesive Protective Member 2-1. Backing (1) Type

Examples of the type of the backing as a component of the pressure-sensitive adhesive protective member (protective member with pressure-sensitive adhesive) in the X-ray detectable adhesive bandage include, but are not limited to, a polyurethane film, a polyester film, a polyvinyl chloride film, an olefin film, a polycarbonate film, a polysulfone film, a polyphenylene sulfide film, a polyimide film, a paper sheet, a fiber-filled film, etc.

The backing may be in any form, such as a mesh material, a woven fabric, or a nonwoven fabric.

For example, a mesh material or a nonwoven fabric used as the backing could form a pressure-sensitive adhesive protective member having an excellent level of cushioning characteristics or air permeability. On the other hand, when a woven fabric of polyester fibers or the like is used as the backing, the water-vapor permeability could be kept low, and the resulting pressure-sensitive adhesive protective member could have good followability to the movement of a finger.

The backing also preferably has an elongation percentage (according to JIS L 1096, hereinafter the same shall apply) of 120% or more, more preferably in the range of 150 to 500%, even more preferably in the range of 200 to 400%, so that good sense of use could be obtained.

However, when the backing to be used has such a high elongation percentage and is difficult to handle, a reinforcing release member is preferably provided on the surface of the backing.

This is because such a reinforcing release member could improve handling ability so that the backing could be easily bonded to the desired place and such a reinforcing release member could also function as a release sheet during manufacture.

The reinforced release member preferably contains a reinforcing material such as fibers or an inorganic filler, or is preferably made thicker than a common release member, or is preferably increased in mechanical strength, since it performs not only as a release member but also as a reinforcing member.

(2) Thickness

The thickness of the backing is preferably in the range of 5 to 2,000 μm.

This is because if the backing has a thickness of below 5 μm, it may have lower mechanical strength or lower handleability and thus may be unsuitable for use in the pressure-sensitive adhesive protective member and other applications.

On the other hand, if the backing has a thickness of above 2,000 μm, it may be too thick and rather difficult to handle, and it may easily peel off from the skin or other parts when used as a component of the pressure-sensitive adhesive protective member or the like.

Thus, the thickness of the backing is more preferably in the range of 10 to 1,000 μm, even more preferably in the range of 15 to 500 μm.

(3) Cushion Layer

Although not shown, a cushion layer made of a nonwoven fabric or the like is preferably provided between the pressure-sensitive adhesive layer and the backing.

This is because such a cushion layer has high ability to protect the affected part and could provide good sense of use. When bumps and dents are formed on the surface of the pressure-sensitive adhesive layer, the cushion layer could also be effective in protecting the shape.

An example of the cushion layer made of a nonwoven fabric or the like is preferably as follows.

Type: urethane resin, polypropylene resin, polyester resin, or vinyl chloride resin Thickness: 10 to 100 μm Weight per area: 10 to 100 g/m²

(4) Water-Repellent-Treated Layer

Although not shown, a water-repellent-treated layer (including a sizing layer) is preferably provided on the surface of the backing.

This is because not only such a layer could easily prevent liquid substances from infiltrating from outside during kitchen work or outside work or in the field of medical care and thus is preferable for sanitary environment, but also such a layer could effectively prevent the pressure-sensitive adhesive protective member from peeling off.

For example, such a water-repellent-treated layer is preferably made of fluororesin, silicone resin, or the like and preferably has a thickness in the range of 0.01 to 5 μm.

(5) Water-Vapor Permeability

The backing preferably has a water-vapor permeability in the range of 100 to 2,000 g/m²·24 hours as measured according to JIS Z 0208.

This is because when the water-vapor permeability of the backing is controlled in this manner, not only liquid substances could be easily prevented from infiltrating from outside during kitchen work or outside work or in the field of medical care, which is preferable for sanitary environment, but also the pressure-sensitive adhesive protective member could be effectively prevented from peeling off.

Thus, the water-vapor permeability of the backing is more preferably in the range of 200 to 1,700 g/m²·24 hours, even more preferably in the range of 400 to 1,400 g/m²·24 hours.

However, when the applications are partially limited, a nonwoven fabric is used as the backing, or open pores are formed in the backing or the pressure-sensitive adhesive layer, the baking preferably has a water-vapor permeability of 1,500 g/m²·24 hours or more as measured according to JIS Z 0208.

(6) Identification Mark and Decorative Layer

Although not shown, an identification mark or a decorative layer is preferably provided on the surface of the backing.

This is because when numeric characters, Chinese characters, pictographs, Braille characters, or other marks are provided, an optimum-sized pressure-sensitive adhesive protective member could be clearly and immediately selected, so that the usability of the pressure-sensitive adhesive protective member could be significantly improved.

Also when such a decorative layer is provided to show numerical patterns, Chinese character patterns, pictograph patterns, photographic patterns, or other patterns, the pressure-sensitive adhesive protective member could have not only improved usability but also higher aesthetic properties. In particular, a fluorescent agent-containing decorative layer could also increase nighttime visibility.

(7) Metal Particle

Figure 5A:
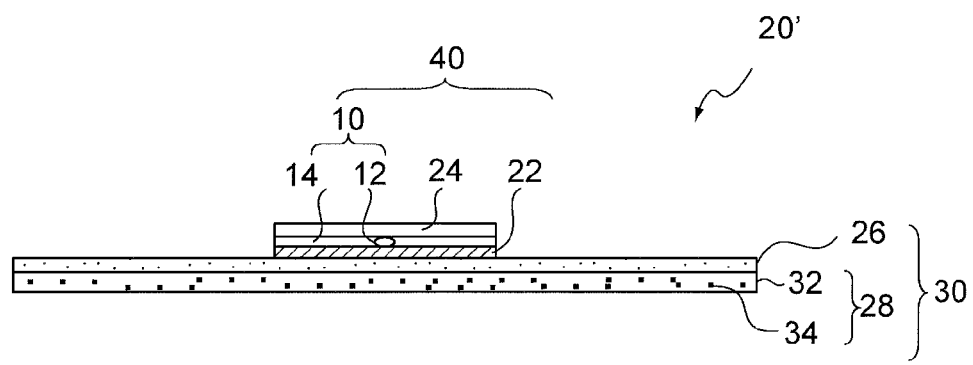
FIGS. 5A to 5C are diagrams provided for illustrating preferred aspects of the X-ray detectable adhesive bandage.

As shown in FIG. 5A, a backing-forming material 32 as a component of the backing 28 in the pressure-sensitive adhesive protective member 30 preferably contains metal particles 34.

This is because such metal particles in the backing could act together with the metal foil and the X-ray detectable material in the absorbent member. Specifically, a metal detector or an X-ray inspection apparatus will be more sensitive to the X-ray detectable adhesive bandage having such an absorbent member and such a pressure-sensitive adhesive protective member.

Even when food products or other products are contaminated by only the backing out of the pressure-sensitive adhesive protective member, the backing containing such metal particles could be detected by a metal detector or an X-ray inspection apparatus under certain conditions.

Although such metal particles may be of any type, for example, such metal particles are preferably made of at least one metal species selected from the group consisting of steel, stainless steel, aluminum, copper, silver, solder (including lead-free solder), and nickel.

This is because according to this feature, the sensitivity of the backing to an X-ray inspection apparatus or a metal detector could be reliably increased, and a relatively inexpensive backing or adhesive bandage could be provided.

It is more preferred to use steel particles, which are inexpensive and have high sensitivity to an X-ray inspection apparatus and a metal detector.

On the other hand, it is also preferred to use aluminum particles, which are lighter, easily dispersible, and inexpensive, and has relatively high sensitivity to an X-ray inspection apparatus and a metal detector.

The metal particles in the backing may be of the same type as the metal in the specific long member. However, if the metal particles in the backing are of a different type from the metal in the specific long member, the sensitivity of the whole adhesive bandage to an X-ray inspection apparatus or a metal detector could be more reliably increased.

The metal particles preferably have an average particle size in the range of 0.5 to 30 μm.

This is because if the metal particles have an average particle size of below 0.5 μm, they may easily aggregate to have significantly lower sensitivity to an X-ray inspection apparatus or a metal detector. On the other hand, if the metal particles have an average particle size of above 30 μm, they may be difficult to be uniformly dispersed in the backing, or may significantly reduce the flexibility or stretchability of the backing.

Thus, the average particle size of the metal particles is more preferably in the range of 3 to 25 μm, even more preferably in the range of 5 to 20 μm.

The content of the metal particles in the backing is preferably in the range of 0.1 to 30% by weight when the total amount of the backing is normalized as 100% by weight.

This is because if the content of the metal particles is below 0.1% by weight, they may have significantly lower sensitivity to an X-ray inspection apparatus or a metal detector. On the other hand, if the content of the metal particles is above 30% by weight, they may be significantly difficult to be dispersed in the backing.

Thus, the content of the metal particles in the backing is more preferably in the range of 1 to 20% by weight, even more preferably in the range of 3 to 15% by weight when the total amount of the backing is normalized as 100% by weight.

(8) Shape

The shape of the pressure-sensitive adhesive protective member is preferably, but not limited to, a long rounded shape as shown in FIG. 1A.

This is because such a shape is convenient to use and could effectively prevent peeling.

Figure 5B:
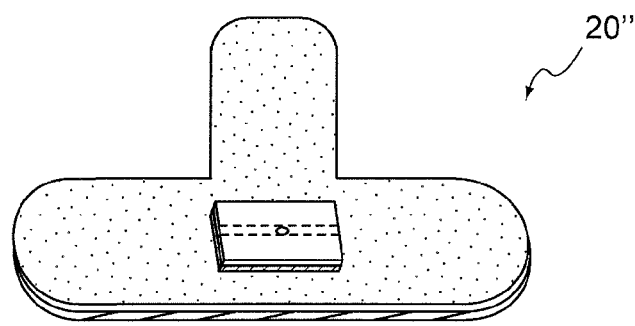
Figure 5C:
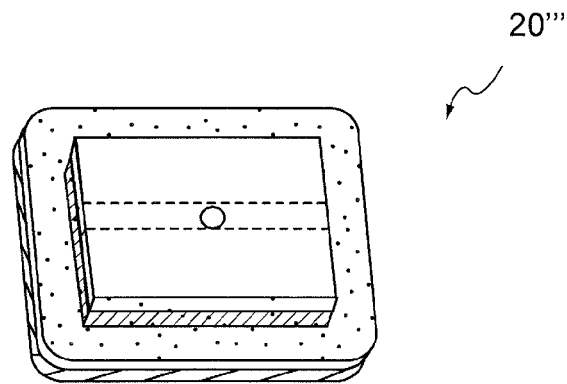

Alternatively, as shown in FIG. 5B, the pressure-sensitive adhesive protective member may have such a shape that it could be easily wound on a fingertip, or as shown in FIG. 5C, it may be of a patch type.

2-2. Pressure-Sensitive Adhesive Layer (1) Type

The pressure-sensitive adhesive layer may be made of any type of pressure-sensitive adhesive. For example, an organopolysiloxane pressure-sensitive adhesive as described below or an acrylic pressure-sensitive adhesive as described below is preferably used.

In the invention, first, an organopolysiloxane pressure-sensitive adhesive is preferably used as a main component of the pressure-sensitive adhesive layer.

This is because the organopolysiloxane pressure-sensitive adhesive used could exhibit moderate adhesion to the skin while it could also improve creep resistance, water resistance, and chemical resistance.

A typical example of such an organopolysiloxane pressure-sensitive adhesive is preferably organopolysiloxane obtained by performing dehydration condensation of a composition containing silicone resin of the structure represented by general formula (1) or (2).

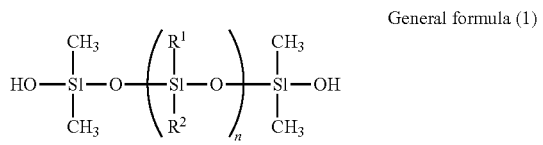

General formula (1)

(In the general formula (1), $R^1$ and $R^2$ each represent a methyl group or a phenyl group and n represents an integer of 10 to 10,000.)

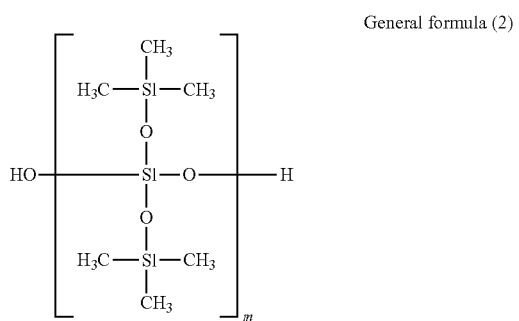

General formula (2)

(In the general formula (2), m represents an integer of 10 to 10,000.)

In the general formula (1), where $R^1$ and $R^2$ are each a methyl group or a phenyl group, the molar ratio of the methyl group to the phenyl group (methyl group/phenyl group) is preferably in the range of 25/75 to 98/2, more preferably in the range of 85/15 to 95/5 so that heat resistance and the like could be imparted to the pressure-sensitive adhesive layer.

Generally, in view of workability in forming the pressure-sensitive adhesive on a fabric, the numbers n and m in the general formulae (1) and (2) are preferably adjusted in such a manner that the pressure-sensitive adhesive could have a viscosity of 2,000 to 200,000 cP (25° C.).

An acrylic pressure-sensitive adhesive is also preferably used as an additive (10 to 30% by weight of the total amount) to the organopolysiloxane pressure-sensitive adhesive or independently (100% by weight of the total amount) of the organopolysiloxane pressure-sensitive adhesive.

This is because the use of such an acrylic pressure-sensitive adhesive makes it possible to easily improve tackiness without reducing the cohesion of the pressure-sensitive adhesive.

A typical example of the type of such an acrylic pressure-sensitive adhesive is an acrylic copolymer composed mainly of 2-ethylhexyl acrylate and butyl acrylate.

To form such a copolymer, the weight ratio of 2-ethylhexyl acrylate to butyl acrylate may be adjusted to 20:80 to 80:20, preferably 20:80 to 40:60. If the content of 2-ethylhexyl acrylate is too low, the cohesion of the pressure-sensitive adhesive may increase, so that the adhesion may decrease. On the other hand, if the content of 2-ethylhexyl acrylate is too high, the cohesion of the pressure-sensitive adhesive may decrease too much, so that the adhesion may tend to decrease.

Acrylamide or vinyl carboxylic acid may also be used as a monomer component in an amount of at most 5% by weight based on the total amount of the monomer components used to form the acrylic pressure-sensitive adhesive.

Also in view of compatibility with the organopolysiloxane pressure-sensitive adhesive, the acrylic pressure-sensitive adhesive preferably has a viscosity in the range of 500 to 20,000 cP (25° C.)

(2) Additive

A preparation (drug) may be added as an additive to the pressure-sensitive adhesive composition so that the desired drug efficacy could be achieved. The type of such a preparation is typically, but not limited to, one or a combination of two or more of an anti-inflammatory agent, an antiphlogistic analgetic, a coronary vasodilator, an asthma agent, an antihypertensive agent, an antihistamine agent, a tranquilizer, an antibiotic, an anesthetic, a vitamin compound, etc.

For example, the content of the preparation is preferably in the range of 0.1 to 30% by weight based on the total amount of the pressure-sensitive adhesive composition, although it depends on the type of the preparation or the intended use of the pressure-sensitive adhesive composition.

Any of various additives are preferably added to the pressure-sensitive adhesive composition. For example, such an additive may be one or a combination of two or more of an antioxidant, a viscosity modifier, an ultraviolet absorbing agent, a masking agent, a plasticizer, a wax, a coloring agent, an inorganic filler, an organic filler, an extender, a coupling agent, etc.

(3) Peel Strength

The peel strength of the adhesive bandage according to JIS Z 0237 (mode: T mode peeling, adherend: stainless steel plate, peel rate: 300 mm/minute) is preferably in the range of 3 to 20 N/25 mm.

This is because if the peel strength is below 3 N/25 mm, the adhesive bandage may easily peel off from the skin or the like and may be poorly functional. On the other hand, if the peel strength is above 20 N/25 mm, the pressure-sensitive adhesive may be difficult to remove from the skin or may be so irritant to the skin that discomfort may occur during use.

Thus, the peel strength of the adhesive bandage is more preferably in the range of 5 to 15 N/25 mm, even more preferably in the range of 9 to 12 N/25 mm.

The peel strength of the adhesive bandage could be adjusted by appropriately selecting the type, thickness, or other properties of the pressure-sensitive adhesive used to form the pressure-sensitive adhesive layer. The following is an aspect of the pressure-sensitive adhesive layer preferred for the control of the peel strength of the adhesive bandage.

Type: organopolysiloxane pressure-sensitive adhesive

Thickness: 10 to 100 μm

Second Embodiment

A second embodiment of the invention is a method of manufacturing an X-ray detectable adhesive bandage 20 including: a pressure-sensitive adhesive protective member 30 including a backing 28 and a pressure-sensitive adhesive layer 26; and an absorbent member 40 that is provided on a predetermined part of the pressure-sensitive adhesive protective member 30 and includes a metal foil 22 provided with a hot melt adhesive layer, a long member 10 including a cover material and an X-ray detectable material entirely or partially covered with the cover material, and an absorbent pad 24, which are sequentially stacked from bottom to top, the method including the following steps (A) to (E).

(A) The step of stacking a metal foil 22 provided with a hot melt adhesive layer, a long member 10 including a cover material 14 and X-ray detectable materials 12 entirely or partially covered with the cover material 14, and an absorbent pad 24 to form an absorbent member 40;
(B) The step of heating the absorbent member 40 to integrate the stacked materials and to form a heat and pressure bonded laminate;
(C) The step of cutting the heat and pressure bonded laminate into pieces of a predetermined size;
(D) The step of forming a pressure-sensitive adhesive protective member 30;
(E) The step of laminating the heat and pressure bonded laminate onto a predetermined part of the pressure-sensitive adhesive protective member 30.

FIG. 6 also illustrates an apparatus 60 for manufacturing an X-ray detectable adhesive bandage 20, which is used in carrying out the method of manufacturing the X-ray detectable adhesive bandage 20 and includes a unit A (mainly for the steps (C), (D), and (E)), a unit B (for a buffering between a unit A and a unit C), and a unit C (mainly for the steps (A) and (B)).

1. Step of Providing Materials

As shown in the unit C of FIG. 6, a specific metal foil 22, a specific long member 10, and an absorbent pad 24 are generally each provided in the form of a roll.

The specific metal foil, the specific long member, and the absorbent pad may each have the features shown in the first embodiment.

Before the long member having X-ray detectable materials arranged at predetermined intervals is used, an infrared sensor, a height (thickness) sensor, an X-ray sensor, or the like is preferably used to check whether the X-ray detectable materials are properly contained.

2. Stacking Step (Step (A))

Subsequently, as shown in the unit C of FIG. 6, the specific metal foil 22, the specific long member 10, and the absorbent pad 24 are sequentially stacked from bottom to top using a laminator, a pressure roll, or the like to form an absorbent member 40.

3. Step of Forming Heat and Pressure Bonded Laminate (Step (B))

Subsequently, as shown in the unit C of FIG. 6, the stacked materials of the absorbent member 40 are integrated using a heat and pressure bonding apparatus 50.

In this step, heat and pressure bonding conditions are not restricted. For example, when the absorbent pad used is a nonwoven fabric of a blend of polyester and rayon fibers, the heat and pressure bonding is preferably performed at a forming temperature higher than the softening point of the polyester fibers (e.g., 240° C.) and lower than the thermal decomposition temperature of the rayon fibers (e.g., about 310° C.).

This is because in the process under such temperature conditions, the polyester fibers serve as a binder for the rayon fibers, so that a heat and pressure bonded laminate having both water absorbency and water repellency could be efficiently produced.

4. Cutting Step (Step (C))

Subsequently, as shown in the unit A of FIG. 6, the absorbent member 40, which is a heat and pressure bonded laminate, is cut into pieces of a predetermined size using a cutting device 53.

After the heating and pressing, the absorbent member may be cut into pieces of a predetermined size using a cutting device, or alternatively, after the lamination, the product may be cut into pieces of a predetermined size and then subjected to heating and pressing.

A cutter, a knife, a laser, a cutting frame, or any other cutting device may be used.

After the absorbent member as a heat and pressure bonded laminate is cut, an infrared sensor, a height (thickness) sensor, an X-ray sensor, or the like is preferably used to check whether the X-ray detectable material is properly contained.

5. Step of Forming Pressure-Sensitive Adhesive Protective Member (Step (D))

Although not shown, a specific backing as a component of the pressure-sensitive adhesive protective member is generally provided in the form of a roll. It may be cut into pieces of a predetermined shape, so that a bandage-forming backing 28 as shown in FIGS. 1A and 1B could be obtained.

A pressure-sensitive adhesive as a component of the pressure-sensitive adhesive protective member is also provided generally in the form of a polymer solution.

The specific backing and the pressure-sensitive adhesive may have the same features as those described in the first embodiment, and therefore repetition of their description will be omitted.

Subsequently, in the step of forming a pressure-sensitive adhesive layer, the polymer solution is applied to the backing, and the applied solution is dried to form a pressure-sensitive adhesive layer.

In this case, the pressure-sensitive adhesive layer may be formed by any method. For example, the pressure-sensitive adhesive composition could be uniformly applied to the backing using a roll coater, a comma coater, a knife coater, or the like.

In the step of forming the pressure-sensitive adhesive layer, a heat treatment is preferably performed under certain conditions to volatilize the solvent or to achieve crosslinking, although it depends on the type of the pressure-sensitive adhesive composition.

The backing 28, on which the pressure-sensitive adhesive layer 26 is formed, is then cut into pieces of a predetermined shape to form a pressure-sensitive adhesive protective member 30.

6. Step of Laminating Pressure-Sensitive Adhesive Protective Member and Heat and Pressure Bonded Laminate (Step (E))

As shown in the unit A of FIG. 6, the resulting pressure-sensitive adhesive protective member 30 and the absorbent member 40, which is the cut piece of the heat and pressure bonded laminate of a predetermined size, are laminated using a laminating apparatus 52 mounted on a support 56, a pressure roll, or the like, so that an X-ray detectable adhesive bandage 20 is obtained.

After the X-ray detectable adhesive bandage 20 is formed, an X-ray sensor 54 or an infrared sensor, a height (thickness) sensor or the like is preferably used to check whether the X-ray detectable material is properly contained.

As shown in the unit B of FIG. 6, a buffering step may be provided between the unit A for performing the step (E) and so on and the unit C for performing the step (A) and so on, so that even when the progress of the operation in the unit A becomes slightly out of sync with that in the unit C, the buffering step could absorb it, and finally the operation in the unit A could be synchronized with that in the unit C.

EXAMPLES

It will be understood that the above embodiments are not intended to limit the invention, and various changes and modifications thereof are possible as needed.

Example 1

1. Preparation of X-Ray Detectable Adhesive Bandage (1) Step of Forming Heat and Pressure Bonded Laminate As shown in FIG. 4B, a 100 μm thick rayon nonwoven fabric was previously folded in a V-shape, and steel wires (2 mm in length, 1 mm in diameter) as X-ray detectable materials were placed at predetermined intervals (25 mm) at the bottom of the V-shape, and surrounded and covered with rayon fibers, so that a long member was obtained.

Subsequently, an aluminum foil (20 μm in thickness) provided with a polyvinyl chloride-based hot melt adhesive, and an absorbent pad (1.5 mm in thickness, 150 g/m$^2$ in weight per area, 0.075 g/cm$^3$ in bulk density) including rayon and polyester fibers and having a network polyethylene film on one side were stacked and subjected to heat and pressure bonding at about 110° C. to form a heat and pressure bonded laminate.

Using a cutter, the heat and pressure bonded laminate was then cut into pieces of a predetermined shape (25 mm in length, 13 mm in width, 100 μm in thickness).

(2) Step of Forming Pressure-Sensitive Adhesive Protective Member

A 30 μm thick urethane film (450% in elongation percentage (according to JIS L 1096) having 720 g/(m$^2$·24 hours) in water-vapor permeability (according to JIS Z 0208)) was provided as a backing.

Also provided was a silicone pressure-sensitive adhesive (7.5 Pa·sec (25° C.) in viscosity, 55.1% by weight in solid content, 12.1 N/25 mm in adhesive strength (according to JIS Z 0237, mode: T mode peeling, adherend: stainless steel plate, peel rate: 300 mm/min)).

The pressure-sensitive adhesive was then applied to the backing using a roll coater, so that a pressure-sensitive adhesive layer with a dry thickness of 25 μm was formed on the backing.

(3) Step of Forming X-Ray Detectable Adhesive Bandage

Subsequently, using a laminator, each resulting heat and pressure bonded laminate was laminated onto a predetermined part of the pressure-sensitive adhesive protective member, so that an X-ray detectable adhesive bandage as shown in FIG. 1A was obtained.

2. Evaluation of X-Ray Detectable Adhesive Bandages (1) X-Ray Detecting Ability (Evaluation 1)

The resulting adhesive bandage was buried in 100 g of potato salad, and it was examined whether or not the buried bandage was detectable as a foreign body by an X-ray inspection apparatus.

Specifically, the resulting adhesive bandages (the number n of samples: 100) were examined for their X-ray detecting ability using an X-ray inspection apparatus KD7305AW (manufactured by Anritsu Industrial Solutions Co., Ltd), and evaluated according to the following criteria.
Very good: The detection result was 100/100 bandages.
Good: The detection result was 98/100 to 99/100 bandages.
Fair: The detection result was 70/100 to 98/100 bandages.
Bad: The detection result was below 70/100 bandages.

(2) Containing Metal Detecting Ability 1 (Evaluation 2)

The resulting adhesive bandage was buried in 100 g of potato salad, and it was examined whether or not the buried bandage was detectable as a foreign body by a metal detector.

Specifically, the resulting adhesive bandages (the number n of samples: 100) were examined for their containing metal detecting ability using a metal detector HA-01 (manufactured by Anritsu Industrial Solutions Co., Ltd), and evaluated according to the following criteria.
Very good: The detection result was 100/100 bandages.
Good: The detection result was 99/100 bandages.
Fair: The detection result was 70/100 to 98/100 bandages.
Bad: The detection result was below 70/100 bandages.

(3) Containing Metal Detecting Ability 2 (Evaluation 3)

The backing (2 cm×1.9 cm in size) of the resulting adhesive bandage was buried in 100 g of potato salad, and it was examined whether or not the buried material was detectable as a foreign body by a metal detector.

Specifically, the backings of the resulting adhesive bandages (the number n of samples: 100) were examined for their containing metal detecting ability using a metal detector HA-01 (manufactured by Anritsu Industrial Solutions Co., Ltd), and evaluated according to the following criteria.
Very good: The detection result was 100/100 backings.
Good: The detection result was 99/100 backings.
Fair: The detection result was 70/100 to 98/100 backings.
Bad: The detection result was below 70/100 backings.

(4) Comfortableness (Evaluation 4)

The comfortableness of the resulting adhesive bandages (the number n of samples: 3) was evaluated according to the following criteria.
Very good: The bandage is sufficiently stretchable and could be very easily put around a finger.
Good: The bandage is almost sufficiently stretchable and could be easily put around a finger.
Fair: The bandage is slightly stretchable and could be put around a finger.
Bad: The bandage is hardly stretchable and difficult to be put around a finger.

(5) Foreign Body Sensation (Evaluation 5)

The resulting adhesive bandage (the number n of samples: 3) was put around a finger when a foreign body sensation to the finger of the X-ray detectable material was evaluated by finger touching according to the following criteria.
Very good: The X-ray detectable material is not felt at all.
Good: The X-ray detectable material is hardly felt.
Fair: The X-ray detectable material is slightly felt.
Bad: The X-ray detectable material is significantly felt.

Examples 2 to 6

In examples 2 to 4, X-ray detectable adhesive bandages were prepared and evaluated in the same manner as in example 1, except that the average length of the wire-shaped X-ray detectable materials in the long member was changed to 2.5 mm, 3.0 mm, and 3.5 mm, respectively and that the thickness of the aluminum foil was changed to 25 μm and 30 μm, respectively, in examples 2 and 3.

In example 5, X-ray detectable adhesive bandages were prepared and evaluated in the same manner as in example 1, except that coiled X-ray detectable materials (2 mm in length, 0.2 mm in thickness) were placed instead in the long member.

In example 6, X-ray detectable adhesive bandages were prepared and evaluated in the same manner as in example 1, except that a 30 μm thick, metal particle-containing, urethane film (metal particles: steel spheres, average particle size: 7 μm, content: 25% by weight, elongation percentage (according to JIS L 1096): 420%, water-vapor permeability (according to JIS Z 0208): 600 g/(m$^2$·24 hours)) was used instead as the backing.

Comparative Example 1

In comparative example 1, X-ray detectable adhesive bandages were prepared and evaluated in the same manner as in example 1, except that the long member exclusive of the X-ray detectable materials was used instead and that the metal foil was not laminated.

Comparative Example 2

In comparative example 2, X-ray detectable adhesive bandages were prepared and evaluated in the same manner as in example 1, except that the steel wire-containing long member was not used and that only the steel wires (4 mm in length, 1 mm in diameter) were disposed in the nonwoven fabric with tweezers.

In most of the adhesive bandages of comparative example 2, however, the steel wire dropped out of the absorbent pad during manufacture or use, which made the manufacture or the use unavailable.

Comparative Example 3

In comparative example 3, X-ray detectable adhesive bandages were prepared and evaluated in the same manner as in example 1, except that the long member containing no X-ray detectable materials was used.

ated to be very low due to the ratio of the number of steel wire-containing samples to the number of samples containing no steel wire.

The adhesive bandages, out of which the steel wire had dropped, could not be subjected to the tests for evaluations 3 and 4. In some adhesive bandages, the shape of the pad was significantly changed by the steel wire, even though they held the steel wire, and such bandages were slightly difficult to be put around a finger. In addition, when the steel wire easily moved in the pad, a foreign body sensation significantly occurred during the application of the bandage to a finger.

The adhesive bandages of comparative example 3 had significantly low sensitivity with respect to the X-ray detecting ability although their containing metal detecting ability was good.

Figure 7:
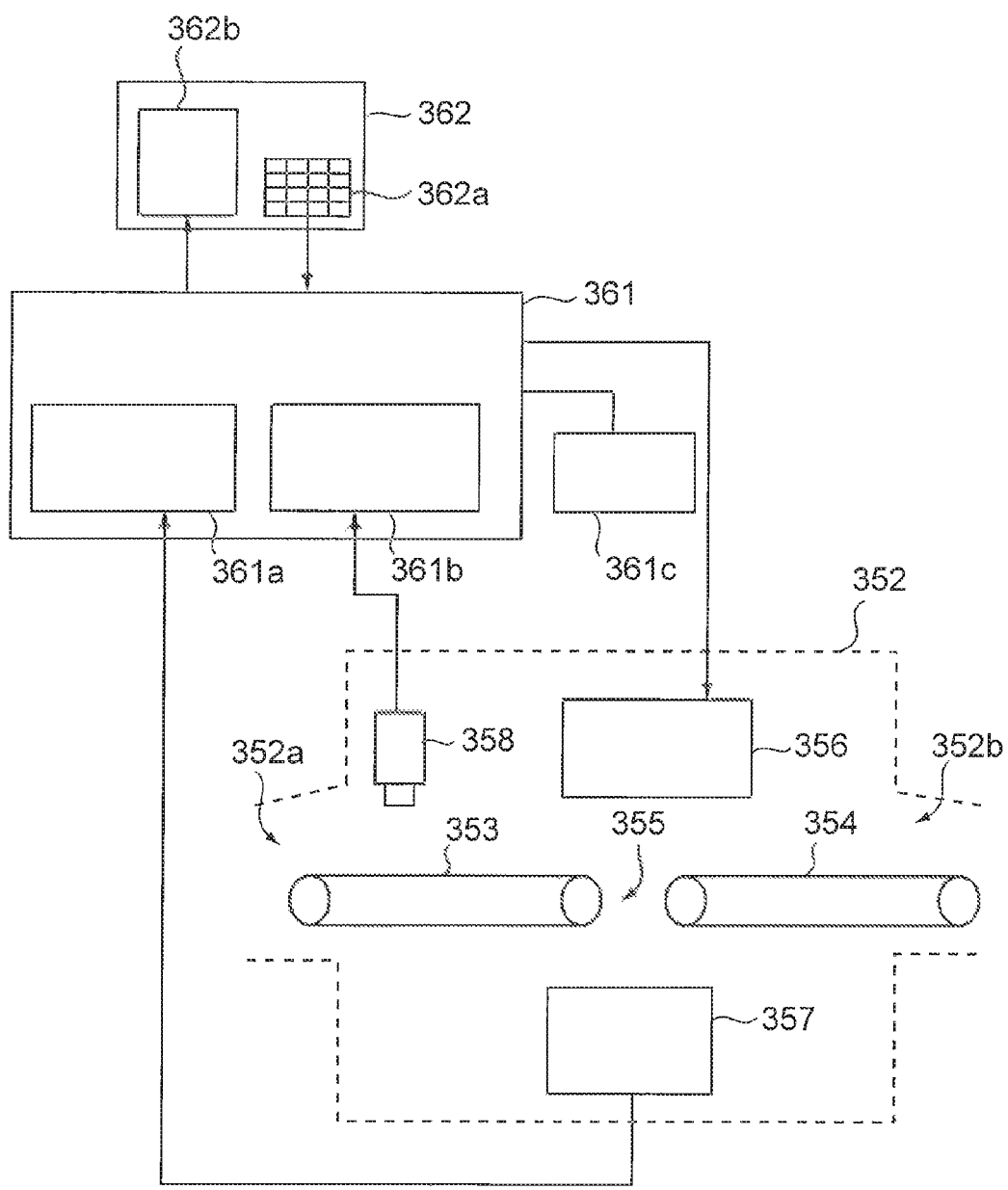
FIG. 7 is a diagram provided for illustrating an X-ray inspection apparatus.
Figure 8A:
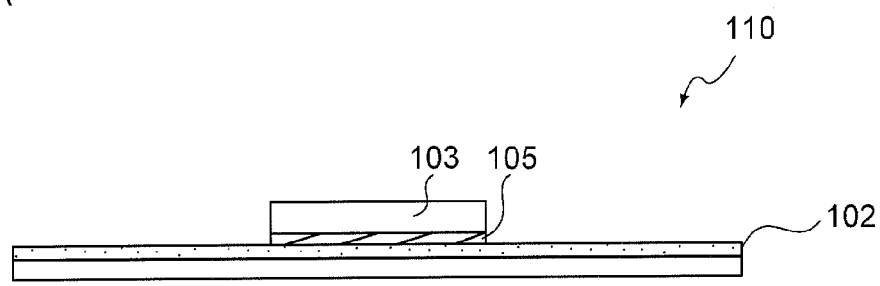
FIGS. 8A to 8B are diagrams provided for illustrating a conventional metal detectable adhesive bandage and a conventional X-ray detectable adhesive bandage.
Figure 8B:
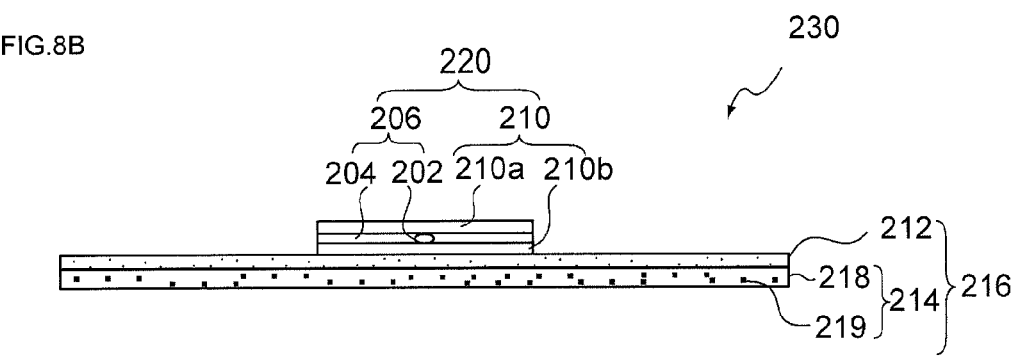

The X-ray detectable adhesive bandage of the invention could be detected with high sensitivity by an X-ray inspection apparatus as shown in FIG. 7, which comprises a controller 361, an X-ray image processing unit 361a, a shape image

TABLE 1

| | X-ray detectable material in long member | | Metal foil | | | | | | |
|---|---|---|---|---|---|---|---|---|---|
| | Type | Average length | Type | Thickness | Evaluation 1 | Evaluation 2 | Evaluation 3 | Evaluation 4 | Evaluation 5 |
| Example 1 | Steel wire | 2.0 mm | Al foil | 20 μm | Very good | Very good | Bad | Very good | Very good |
| Example 2 | Steel wire | 2.5 mm | Al foil | 25 μm | Very good | Very good | Bad | Very good | Very good |
| Example 3 | Steel wire | 3.0 mm | Al foil | 30 μm | Very good | Very good | Bad | Very good | Good |
| Example 4 | Steel wire | 3.5 mm | Al foil | 20 μm | Very good | Very good | Bad | Very good | Good |
| Example 5 | Steel wire | 2.0 mm | Al foil | 20 μm | Very good | Very good | Bad | Good | Fair |
| Example 6 | Steel wire | 3.5 mm | Al foil | 20 μm | Very good | Very good | Good | Very good | Good |
| Comparative Example 1 | Absent | Absent | Absent | Absent | Bad | Bad | Bad | Very good | Very good |
| Comparative Example 2 | Steel wire | 4.0 mm | Al foil | 20 μm | Bad | Very good | Bad | Fair | Bad |
| Comparative Example 3 | Absent | Absent | Al foil | 20 μm | Bad | Very good | Bad | Very good | Very good |

*In Comparative Example 2, the steel wire containing the long member was not used and only the steel wire was disposed in the pad with tweezers.

As shown in Table 1, the adhesive bandages of examples 1 to 6 all had the X-ray detecting ability (Evaluation 1) of high sensitivity and the containing metal detecting ability (Evaluations 2 and 3) of high sensitivity and all showed good results on comfortableness (Evaluation 4) and foreign body sensation (Evaluation 5). The adhesive bandages of examples 1 to 6 were detectable with high accuracy not only by an X-ray inspection apparatus but also by a metal detector.

On the other hand, the adhesive bandage of comparative example 1 had significantly low sensitivity with respect to the X-ray detecting ability, although it showed good results on the containing metal detecting ability, comfortableness and foreign body sensation.

Among the adhesive bandages (100 samples) obtained under the conditions of comparative example 2, the adhesive bandages each containing the steel wire in the absorbent pad (about ⅓ of all samples) had very good sensitivity to the X-ray inspection apparatus and the metal detector. However, most of the resulting adhesive bandages (about ⅔ of all samples) caused the steel wire to drop out of the absorbent pad during manufacture or test, and these adhesive bandages had significantly low sensitivity to the X-ray inspection apparatus and the metal detector. Thus, the X-ray detecting ability and the containing metal detecting ability (Evaluation 2) per 100 adhesive bandages of comparative example 2 were evaluated to be very low due to the ratio of the number of steel processing unit 361b, a storage unit 361c, an X-ray irradiator 356, and an X-ray detector 357. Thus, the X-ray detectable adhesive bandage of the invention is expected to be applicable as a marker for food products, fiber products, clothes, and small articles, for which foreign body contamination and marker's performance are issues, and also expected to be applicable as a marker for documents, a marker for electric appliances, a tag for footwear, a tag for mechanical devices, etc.

Thus, even when the X-ray detectable adhesive bandage is accidentally placed in a product packaged in metal, it could be detected by an X-ray inspection apparatus, so that foreign body contamination could be easily prevented.

In addition, the X-ray detectable adhesive bandage of the invention, in which the heat and pressure bonded laminate includes an X-ray detectable material and a metal foil, is detectable with high sensitivity not only by an X-ray inspection apparatus but also by a metal detector.

DESCRIPTION OF REFERENCE SIGNS

10: Long member, 12, 12': X-ray detectable material, 14: Cover material, 20, 20', 20'', 20''': X-ray detectable adhesive bandage, 22: Metal foil, 24: Absorbent pad, 26: Pressure-sensitive adhesive layer, 28: Backing, 30: Pressure-sensitive adhesive protective member, 32, 218:

Backing-forming material, 34, 219: Metal particles, 40: Absorbent member (heat and pressure bonded laminate)

What is claimed is:

1. An X-ray detectable adhesive bandage comprising:
  a pressure-sensitive adhesive protective member comprising a backing and a pressure-sensitive adhesive layer; and
  an absorbent member that is provided on a predetermined part of the pressure-sensitive adhesive protective member and comprises a metal foil provided with a hot melt adhesive layer, a long member comprising a cover material and an X-ray detectable material entirely or partially covered with the cover material, and an absorbent pad, wherein the metal foil, the long member, and the absorbent pad are sequentially stacked from bottom to top, wherein
  the absorbent member comprises a heat and pressure bonded laminate of the metal foil provided with the hot melt adhesive layer, the long member comprising the cover material and the X-ray detectable material entirely or partially covered with the cover material, and the absorbent pad.

2. The X-ray detectable adhesive bandage according to claim 1, wherein the X-ray detectable material is linear and has an average length in a range of 0.3 mm to 10 mm and an average thickness in a range of 0.1 mm to 3 mm.

3. The X-ray detectable adhesive bandage according to claim 1, wherein the X-ray detectable material is a coiled material.

4. The X-ray detectable adhesive bandage according to claim 1, wherein the metal foil is made of aluminum.

5. The X-ray detectable adhesive bandage according to claim 1, wherein the metal foil has a thickness in a range of 1 µm to 30 µm.

6. The X-ray detectable adhesive bandage according to claim 1, wherein the hot melt adhesive is at least one selected from the group consisting of an olefin-based hot melt adhesive, a polyethylene-based hot melt adhesive, a polypropylene-based hot melt adhesive, a polyester-based hot melt adhesive, and a polyvinyl chloride-based hot melt adhesive.

7. The X-ray detectable adhesive bandage according to claim 1, wherein the backing in the pressure-sensitive adhesive protective member is colored.

8. A method for manufacturing an X-ray detectable adhesive bandage comprising: a pressure-sensitive adhesive protective member comprising a backing and a pressure-sensitive adhesive layer; and an absorbent member that is provided on a predetermined part of the pressure-sensitive adhesive protective member and comprises a metal foil provided with a hot melt adhesive layer, a long member comprising a cover material and an X-ray detectable material entirely or partially covered with the cover material, and an absorbent pad, all of which are sequentially stacked from bottom to top, the method comprising the steps of:
  stacking the metal foil, the long member comprising the cover material and X-ray detectable material entirely or partially covered with the cover material, and the absorbent pad;
  heating the absorbent member to integrate the stacked materials and to form a heat and pressure bonded laminate;
  cutting the heat and pressure bonded laminate into pieces of a predetermined size;
  forming the pressure-sensitive adhesive protective member; and
  laminating the heat and pressure bonded laminate onto a predetermined part of the pressure-sensitive adhesive protective member.

* * * * *